(12) United States Patent
Schuhmann et al.

(10) Patent No.: US 12,649,706 B2
(45) Date of Patent: Jun. 9, 2026

(54) PROCESS FOR PRODUCING PURE METHANOL FROM A CARBON DIOXIDE-RICH SYNTHESIS GAS WITH SINGLE COLUMN PURIFICATION

(71) Applicant: L'Air Liquide Société Anonyme pour l'Etude et l'Exploitation des Procédés Georges Claude, Paris (FR)

(72) Inventors: Timm Schuhmann, Bensheim (DE); Tobias Oelmann, Bad Vilbel (DE); Michael Wilken, Frankfurt am Main (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 492 days.

(21) Appl. No.: 18/142,631

(22) Filed: May 3, 2023

(65) Prior Publication Data

US 2023/0357111 A1     Nov. 9, 2023

(30) Foreign Application Priority Data

May 3, 2022    (EP) .................................... 22020204

(51) Int. Cl.
| | |
|---|---|
| *C07C 29/15* | (2006.01) |
| *C07C 29/151* | (2006.01) |
| *C07C 29/80* | (2006.01) |

(52) U.S. Cl.
CPC .......... *C07C 29/1516* (2013.01); *C07C 29/80* (2013.01)

(58) Field of Classification Search
CPC ....... C07C 29/15; C07C 29/151; C07C 29/80; C07C 31/04
See application file for complete search history.

(56) References Cited

U.S. PATENT DOCUMENTS

| | | | | |
|---|---|---|---|---|
| 5,346,593 | A | * | 9/1994 | Cialkowski ............ B01D 3/146 203/99 |
| 2011/0214981 | A1 | * | 9/2011 | Early .................... C07C 29/151 203/37 |
| 2021/0300852 | A1 | * | 9/2021 | Gronemann ............ C07C 29/80 |

OTHER PUBLICATIONS

European Search Report and Written Opinion for corresponding EP 22020204.8, Nov. 14, 2022.

* cited by examiner

*Primary Examiner* — Yate' K Cutliff
(74) *Attorney, Agent, or Firm* — Elwood L. Haynes

(57) ABSTRACT

Provided is a process for producing pure methanol from carbon dioxide-rich synthesis gas, the process including the following steps: at least partially reacting the carbon dioxide rich synthesis gas in a methanol synthesis unit, discharging a liquid crude methanol stream from the methanol synthesis unit, introducing the liquid crude methanol stream into a flash tank, discharging from the flash tank a liquid depressurized crude methanol stream as a bottoms product and a gaseous overhead product stream having synthesis gas components, introducing the liquid depressurized crude methanol stream into a distillation apparatus having of a single distillation column, separating the crude methanol stream in the distillation column, discharging an overhead product stream via an overhead product outlet, discharging a bottoms product stream via the bottoms product outlet, and discharging a pure methanol product stream via a first side draw.

13 Claims, 5 Drawing Sheets

Figure 3A:
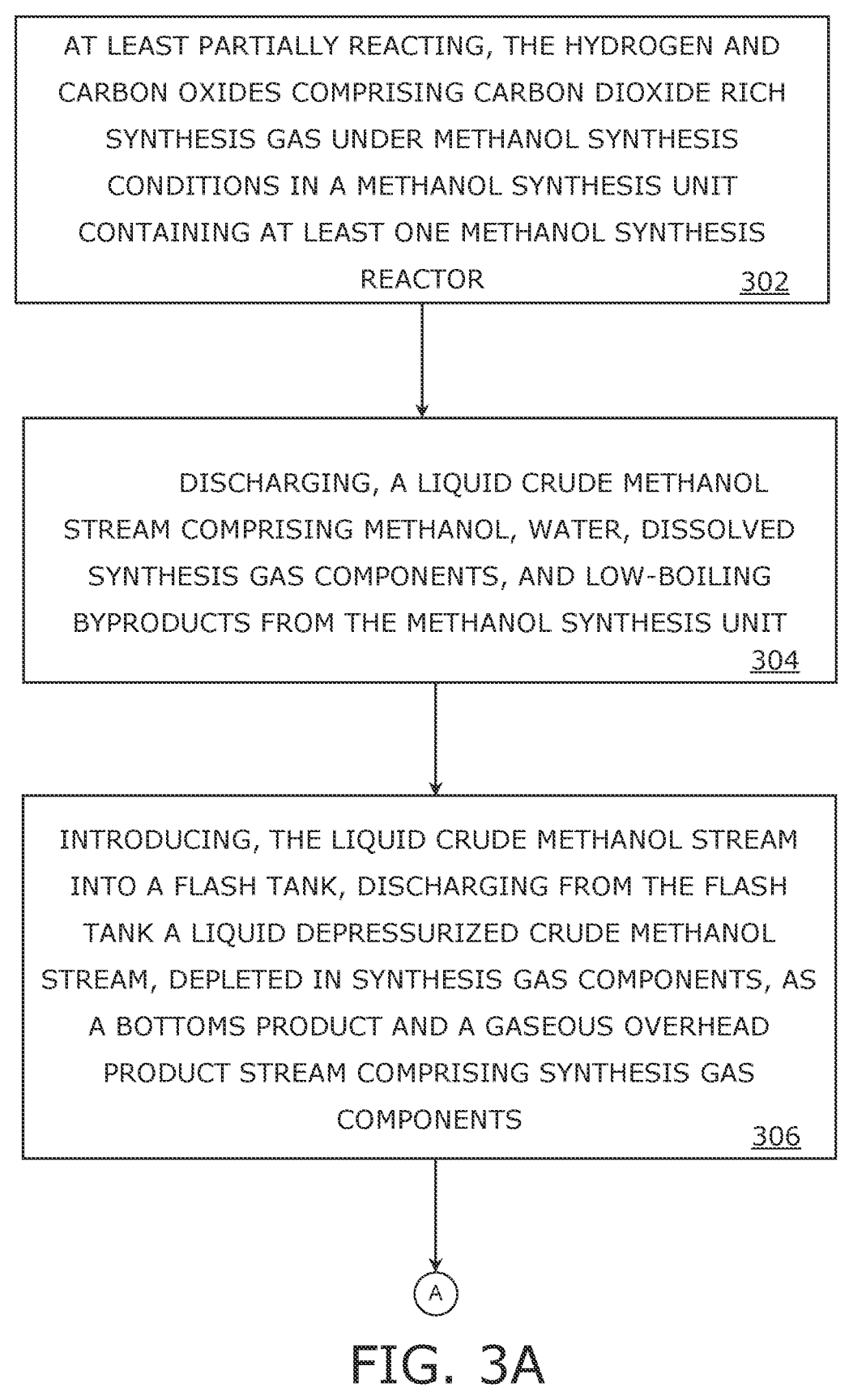

AT LEAST PARTIALLY REACTING, THE HYDROGEN AND CARBON OXIDES COMPRISING CARBON DIOXIDE RICH SYNTHESIS GAS UNDER METHANOL SYNTHESIS CONDITIONS IN A METHANOL SYNTHESIS UNIT CONTAINING AT LEAST ONE METHANOL SYNTHESIS REACTOR          302

DISCHARGING, A LIQUID CRUDE METHANOL STREAM COMPRISING METHANOL, WATER, DISSOLVED SYNTHESIS GAS COMPONENTS, AND LOW-BOILING BYPRODUCTS FROM THE METHANOL SYNTHESIS UNIT          304

INTRODUCING, THE LIQUID CRUDE METHANOL STREAM INTO A FLASH TANK, DISCHARGING FROM THE FLASH TANK A LIQUID DEPRESSURIZED CRUDE METHANOL STREAM, DEPLETED IN SYNTHESIS GAS COMPONENTS, AS A BOTTOMS PRODUCT AND A GASEOUS OVERHEAD PRODUCT STREAM COMPRISING SYNTHESIS GAS COMPONENTS          306

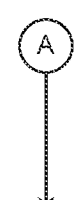

INTRODUCING, THE LIQUID DEPRESSURIZED CRUDE METHANOL STREAM DEPLETED IN SYNTHESIS GAS COMPONENTS INTO A DISTILLATION APPARATUS CONSISTING OF A SINGLE DISTILLATION COLUMN, THE DISTILLATION COLUMN COMPRISING A CRUDE METHANOL INLET, AN OVERHEAD PRODUCT OUTLET AT THE TOP OF THE COLUMN, A BOTTOMS PRODUCT OUTLET AT THE BOTTOM OF THE COLUMN, AND A FIRST SIDE DRAW, THE FIRST SIDE DRAW IS LOCATED IN THE RECTIFYING SECTION OF THE DISTILLATION COLUMN

308

SEPARATING, THE CRUDE METHANOL STREAM BY DISTILLATION IN THE DISTILLATION COLUMN UNDER DISTILLATION CONDITIONS

310

FIG. 3B

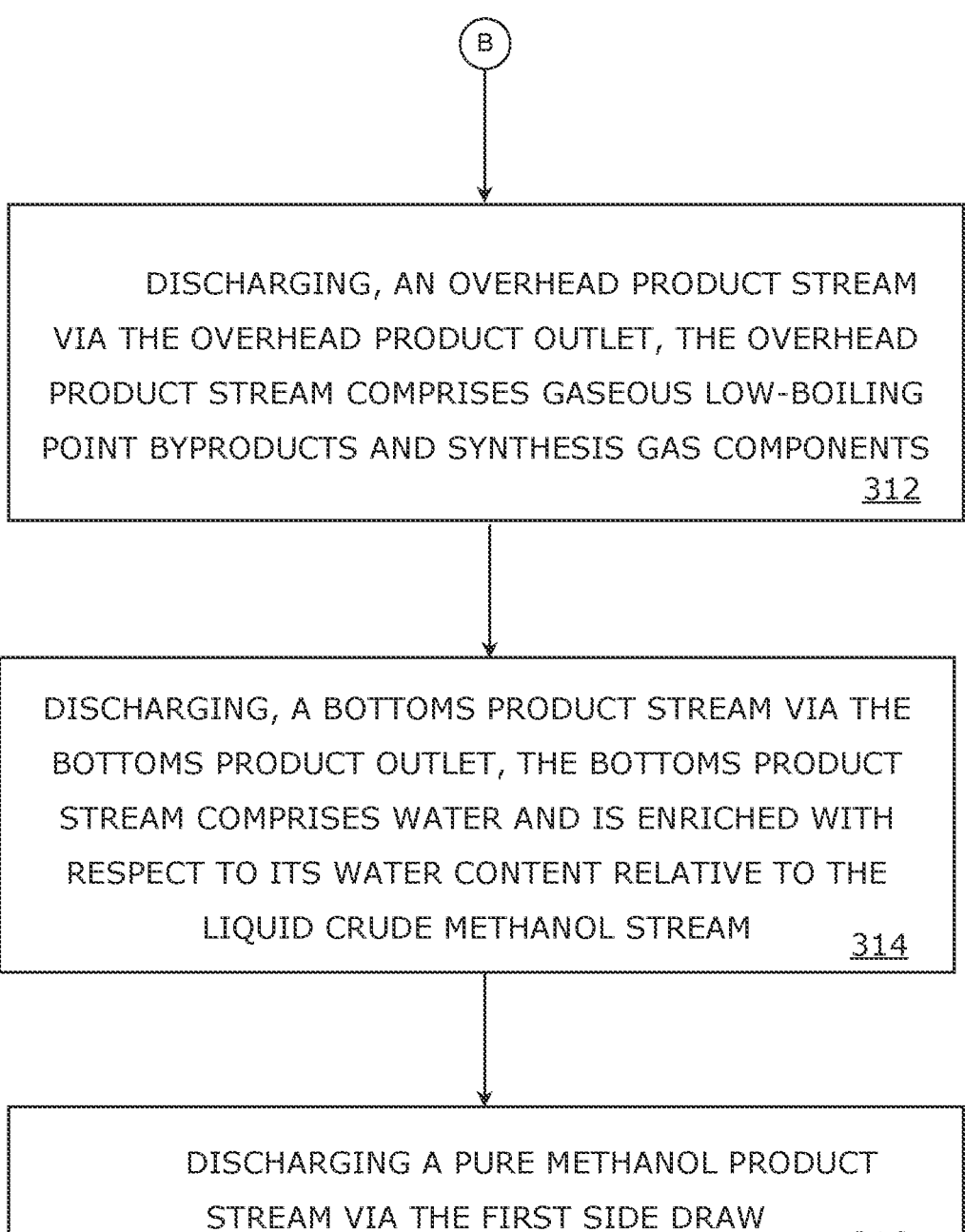

DISCHARGING, AN OVERHEAD PRODUCT STREAM VIA THE OVERHEAD PRODUCT OUTLET, THE OVERHEAD PRODUCT STREAM COMPRISES GASEOUS LOW-BOILING POINT BYPRODUCTS AND SYNTHESIS GAS COMPONENTS
312

DISCHARGING, A BOTTOMS PRODUCT STREAM VIA THE BOTTOMS PRODUCT OUTLET, THE BOTTOMS PRODUCT STREAM COMPRISES WATER AND IS ENRICHED WITH RESPECT TO ITS WATER CONTENT RELATIVE TO THE LIQUID CRUDE METHANOL STREAM
314

DISCHARGING A PURE METHANOL PRODUCT STREAM VIA THE FIRST SIDE DRAW
316

FIG. 3C

PROCESS FOR PRODUCING PURE METHANOL FROM A CARBON DIOXIDE-RICH SYNTHESIS GAS WITH SINGLE COLUMN PURIFICATION

CROSS REFERENCE TO RELATED APPLICATIONS

This application claims the benefit of priority under 35 U.S.C. § 119 (a) and (b) to European Patent Application No. 22020204.8, filed May 3, 2022, the entire contents of which are incorporated herein by reference.

TECHNICAL FIELD

The present disclosure relates generally to methanol production; more specifically, the present disclosure relates to a process for producing pure methanol from a carbon dioxide-($CO_2$)-rich synthesis gas with single column purification.

BACKGROUND

Over the years, several processes have been developed in order to maximize methanol yield and selectivity and minimize byproduct formation. Typical byproducts (in weight (wt.)-parts per million (ppm)) in crude methanol for different synthesis gases as raw materials for methanol synthesis are shown in the following table for the following cases:

Case "$CO_2$": 24 vol % "$CO_2$" in synthesis gas with high $CO_2$ content;

Case "NG" (=natural gas): 8 vol % "$CO_2$" in synthesis gas;

Case "Coal": 2 vol % "$CO_2$" in synthesis gas.

The methanol is conventionally purified in a two or three stage column arrangement. The light boilers or dissolved gases are boiled in the so-called pre-run column and the stabilized methanol thus obtained is fed into a product column. In this process, methanol is separated from water. The design criterion, however, is the ethanol content in the methanol product, which must be below 10 wt.-ppm according to Grade AA specifications (US Federal Specification O-M-232N, Methanol).

| Byproducts | Case $CO_2$ | Case NG | Case COAL |
|---|---|---|---|
| Dimethyl Ether (DME) | 27 | 80 | 660 |
| Hydro Carbon (HC) | 0 | 71 | 284 |
| Ethanol (ETOH) | 70 | 515 | 1600 |
| Iso-Propanol | 25 | 180 | 705 |
| Butanol | 12 | 230 | 615 |
| Methyl Formate (MFOR) | 500 | 600 | 1295 |
| OTHERS | 0 | 107 | 670 |
| TOTAL | 634 | 1783 | 5829 |

Using a single column methanol purification system for purification of methanol produced from conventional synthesis gases derived from e. g. coal or natural gas (NG), it is not possible to produce pure methanol of Grade A or even AA under economically justifiable condition, and it can therefore be used only in plants which are scheduled to turn out methanol for burner fuel or motor fuel applications. Further due to high ethanol content in conventional synthesis gas, a single column purification system is not economical. With a two-column methanol purification system, there are high investment costs for the columns, but also for evaporators and condensers as well as instrumentation and other related costs. However, the lower byproduct concentration of crude methanol produced from synthesis gases with a high $CO_2$ content may open new opportunities to simplify purification.

Therefore, there is a need to address the aforementioned technical drawbacks in existing technologies for a simple and an economic process for producing pure methanol from a carbon dioxide-rich synthesis gas.

SUMMARY

The present disclosure seeks to provide a process for producing pure methanol from a carbon dioxide-rich synthesis gas where the capital costs are dominant in determining the overall economics. The present disclosure aims to provide a solution that overcomes, at least partially, the problems encountered in the prior art and provide an improved process for the purification of crude methanol from the synthesis gas with only one distillation column. A simple integration of a side draw in a product column, produces a methanol product meeting the specification completely without an upstream pre-run column, thus using only a single distillation column for methanol production. The object of the present disclosure is achieved by the solutions provided in the enclosed independent claims. Advantageous implementations of the present disclosure are further defined in the dependent claims.

According to a first aspect, the present disclosure provides a process for producing pure methanol from a carbon dioxide-rich synthesis gas containing hydrogen and carbon oxides as synthesis gas components, comprising the following steps:

(a) at least partially reacting the hydrogen and carbon oxides comprising carbon dioxide-rich synthesis gas under methanol synthesis conditions in a methanol synthesis unit containing at least one methanol synthesis reactor, (b) discharging a liquid crude methanol stream comprising methanol, water, dissolved synthesis gas components, and low-boiling byproducts from the methanol synthesis unit, (c) introducing the liquid crude methanol stream into a flash tank, discharging from the flash tank a liquid depressurized crude methanol stream, depleted in synthesis gas components, as a bottoms product and a gaseous overhead product stream comprising synthesis gas components, (d) introducing the liquid depressurized crude methanol stream depleted in synthesis gas components into a distillation apparatus consisting of a single distillation column, the distillation column comprising a crude methanol inlet, an overhead product outlet at the top of the column, a bottoms product outlet at the bottom of the column, and a first side draw, wherein the first side draw is located in the rectifying section of the distillation column, (e) separating the crude methanol stream by distillation in the distillation column under distillation conditions, (f) discharging an overhead product stream via the overhead product outlet, wherein the overhead product stream comprises gaseous low-boiling point byproducts and synthesis gas components, (g) discharging a bottoms product stream via the bottoms product outlet, wherein the bottoms product stream comprises water and is enriched with respect to its water content relative to the liquid crude methanol stream, and (h) discharging a pure methanol product stream via the first side draw.

The process for producing pure methanol from the carbon dioxide-rich synthesis gas containing hydrogen and carbon oxides as synthesis gas components according to the present disclosure enables purification of crude methanol from the synthesis gas with only one distillation column. The process enables producing a methanol product meeting the specification completely without an upstream pre-run column. The process enables a single distillation column to be used for the purification of crude methanol by integrating a side draw in the product column instead of a two- or three-stage column arrangement used in conventional methanol synthesis processes, thus providing an economic advantage of significantly lowering investment costs for the purification of crude methanol in methanol production facilities. The calculated concentrations of methyl formate in the methanol product produced by the process of the present disclosure showed no influence on the acidity and thus on the specification of the methanol in the laboratory.

Embodiments of the present disclosure eliminate the aforementioned drawbacks in existing known approaches for producing pure methanol from a carbon dioxide-rich synthesis gas with a single column purification by integrating a side draw in the product column. The advantage of the embodiments according to the present disclosure is that the embodiments enable producing a methanol product meeting the specification completely without an upstream pre-run column, thus providing an economic advantage of significantly lowering investment costs for the purification of crude methanol in methanol production facilities.

Additional aspects, advantages, features, and objects of the present disclosure are made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. To illustrate the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, the same elements have been indicated by identical numbers. Embodiments of the present disclosure will now be described, by way of example only, with reference to the following diagrams wherein:

FIG. 3A is a flowchart illustrating a process for producing pure methanol from a carbon dioxide-rich synthesis gas containing hydrogen and carbon oxides as synthesis gas components according to an embodiment of the present disclosure.

FIG. 3B is a flowchart illustrating a process for producing pure methanol from a carbon dioxide-rich synthesis gas containing hydrogen and carbon oxides as synthesis gas components according to an embodiment of the present disclosure.

FIG. 3C is a flowchart illustrating a process for producing pure methanol from a carbon dioxide-rich synthesis gas containing hydrogen and carbon oxides as synthesis gas components according to an embodiment of the present disclosure.

DETAILED DESCRIPTION OF PREFERRED EMBODIMENTS

Figure 1:
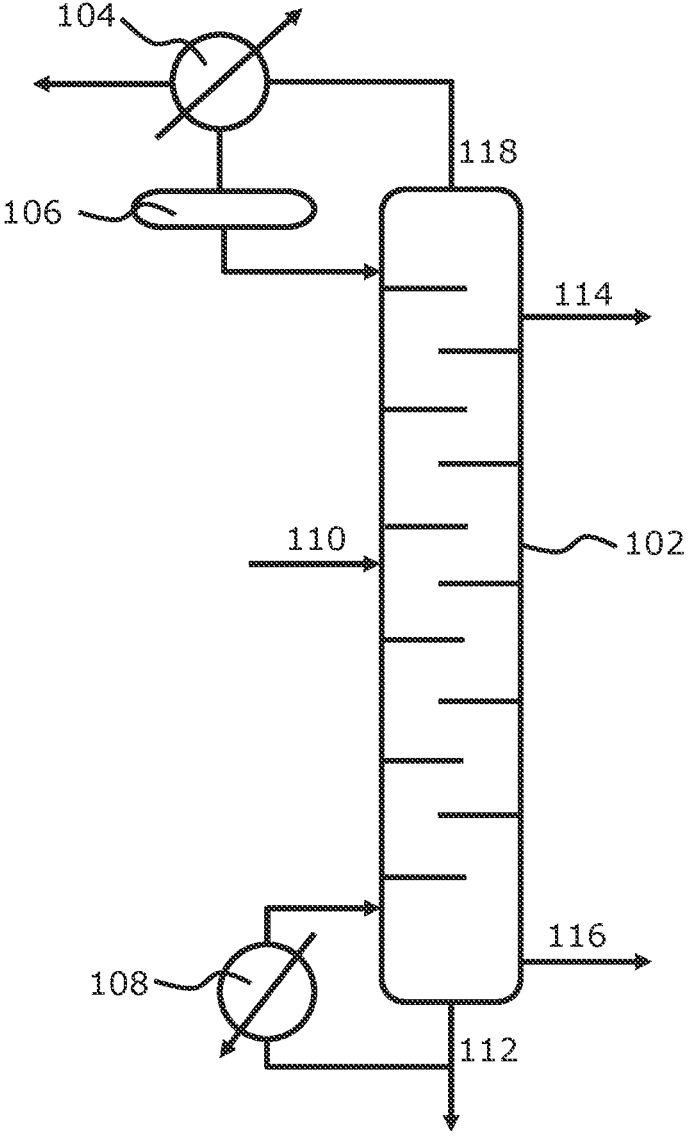
FIG. 1 is a schematic illustration of a distillation apparatus of a process plant for producing pure methanol from a carbon dioxide-rich synthesis gas according to an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The conditions required for performing methanol synthesis are known to the skilled person from the prior art. These are the physicochemical conditions under which a measurable, at least partial, preferably an industrially relevant, conversion of synthesis gas components to a methanol product is achieved. In this sense "at least partially reacting" is to be understood as subjecting educts to physicochemical conditions that cause such an at least partial conversion, preferably a technically and economically relevant conversion. Necessary adjustments of these conditions to the respective operational requirements will be made on the basis of routine experiments. Any specific reaction conditions disclosed may serve here as a guide, but they should not be regarded as limiting in relation to the scope of the invention.

Similarly, the distillation conditions for separating the crude methanol stream by distillation are known to the skilled person from the prior art. These are the physicochemical conditions under which a separation or fractionation of the crude methanol stream is performed in order to obtain at least two distillation fractions or products with a higher and with a lower methanol content relative to the crude methanol stream. Also, with regard to the distillation conditions, necessary adjustments will be made by the skilled on the basis of routine experiments. Any specific distillation conditions disclosed may serve here as a guide, but they should not be regarded as limiting in relation to the scope of the invention.

In the context of the distillation, low-boiling and high-boiling products are to be understood to designate boiling points or boiling point ranges of distillation educts or products, pure components or component mixtures, or material streams relative to the boiling point of methanol under the specific distillation conditions.

According to the stoichiometry of the methanol synthesis reaction for synthesis gas comprising only carbon monoxide (CO), but no carbon dioxide ($CO_2$):

$$2H_2 + CO = CH_3OH$$

an $H_2/CO$ ratio of at least 2 is required under practical synthesis conditions, often even slightly greater than 2, for example 2.1. This ratio is typically formulated as the stoichiometry number SN of the methanol synthesis and takes into account that carbon dioxide too reacts to afford methanol: $SN=([H_2]-[CO_2])/([CO]+[CO_2])$.

A means is to be understood as meaning something that enables or is helpful in the achievement of a goal. In particular, means for performing a particular process step are to be understood as including all physical articles that would be considered by a person skilled in the art in order to be able to perform this process step. For example, a person skilled in the art will consider means of introducing or discharging a material stream to include all transporting and conveying apparatuses, i.e., for example pipe-lines, pumps, compressors, valves, which seem necessary or sensible to said skilled person for performance of this process step on the basis of his knowledge of the art.

Pressure indications are in bar, absolute, bar(a) or bara for short, unless otherwise stated in the particular context.

According to a first aspect, the present disclosure provides a process for producing pure methanol from a carbon dioxide-rich synthesis gas containing hydrogen and carbon oxides as synthesis gas components, comprising the following steps: (a) at least partially reacting the hydrogen and carbon oxides comprising carbon dioxide rich synthesis gas under methanol synthesis conditions in a methanol synthesis unit containing at least one methanol synthesis reactor, (b) discharging a liquid crude methanol stream comprising methanol, water, dissolved synthesis gas components, and low-boiling byproducts from the methanol synthesis unit, (c) introducing the liquid crude methanol stream into a flash tank, discharging from the flash tank a liquid depressurized crude methanol stream, depleted in synthesis gas components, as a bottoms product and a gaseous overhead product stream comprising synthesis gas components, (d) introducing the liquid depressurized crude methanol stream depleted in synthesis gas components into a distillation apparatus consisting of a single distillation column, the distillation column comprising a crude methanol inlet, an overhead product outlet at the top of the column, a bottoms product outlet at the bottom of the column, and a first side draw, wherein the first side draw is located in the rectifying section of the distillation column, (e) separating the crude methanol stream by distillation in the distillation column under distillation conditions, (f) discharging an overhead product stream via the overhead product outlet, wherein the overhead product stream comprises gaseous low-boiling point byproducts and synthesis gas components, (g) discharging a bottoms product stream via the bottoms product outlet, wherein the bottoms product stream comprises water and is enriched with respect to its water content relative to the liquid crude methanol stream, and (h) discharging a pure methanol product stream via the first side draw.

The process for producing pure methanol from a carbon dioxide-rich synthesis gas containing hydrogen and carbon oxides as synthesis gas components according to the present disclosure enables purification of crude methanol from the synthesis with only the single distillation column. The process enables producing a pure methanol product meeting the specification completely without an upstream pre-run column. The process enables the single distillation column to be used for the purification of crude methanol by integrating a side draw in the product column instead of a two or three stage column arrangement used in conventional methanol processes, thus providing an economic advantage for the purification of crude methanol in methanol production facilities. The calculated concentrations of methyl formate in the methanol product produced by the process of the present disclosure showed no influence on the acidity and thus on the specification of the methanol in the laboratory.

Optionally, in the carbon dioxide-rich synthesis gas the concentration of carbon dioxide is greater than the concentration of carbon monoxide. The raw methanol produced in addition to water from the synthesis gas with a high $CO_2$ content contains a considerably lower proportion of byproducts than in the case of conventional synthesis gases comprising less $CO_2$ but more CO.

Optionally, in the carbon dioxide-rich synthesis gas the concentration of carbon monoxide is at most 4 mol.-%.

Optionally, in the carbon dioxide-rich synthesis gas the concentration of carbon dioxide is at least 15 mol.-%, preferably at least 20 mol.-%.

Optionally, the stoichiometry number of the carbon dioxide-rich synthesis gas is between 1.8 and 2.4, preferably between 1.95 and 2.2, most preferably between 1.98 and 2.0.

Optionally, the methanol concentration in the pure methanol product stream is at least 99.85 wt.-% on a dry basis.

Optionally, the concentration of methyl formate in the crude methanol is at most 2000 wt.-ppm, preferably at most 1000 wt.-ppm, most preferably at most 500 wt.-ppm. Optionally, the distillation column comprises at least 30 theoretical plates, preferably at least 40 theoretical plates.

Optionally, the distillation column is operated at 1 to 5 bara, preferably at 1 to 2 bara, most preferably at atmospheric pressure.

Optionally, the first side draw is arranged at most 10 theoretical plates, preferably at most 5 theoretical plates below the overhead product outlet.

Optionally, the distillation column comprises a second side draw, wherein the second side draw is arranged in the stripping section of the distillation column.

Optionally, the second side draw is arranged at most 10 theoretical plates, preferably at most 5 theoretical plates above the bottoms product outlet.

Optionally, an ethanol containing high-boiling product stream is discharged from the distillation column via the second side draw.

Optionally, the ethanol concentration in the high-boiling product stream is at most 10 mol.-%, preferably at most 5 mol.-%.

Optionally, the methanol concentration in the high-boiling product stream is at least 25 mol.-%, preferably at least 35 mol.-%, most preferably at least 45 mol.-%.

Embodiments of the present disclosure substantially eliminate or at least partially address the aforementioned technical drawbacks in existing technologies in providing a process for producing pure methanol from a carbon dioxide-rich synthesis gas containing hydrogen and carbon oxides as synthesis gas components where the capital costs are dominant in determining the overall economics.

FIG. 1 is a schematic illustration of a distillation apparatus 100 of a process plant for producing pure methanol from a carbon dioxide-rich synthesis gas according to an embodiment of the present disclosure. The carbon dioxide-rich synthesis gas includes hydrogen and carbon oxides as synthesis gas components. The distillation apparatus 100 includes a single distillation column 102, a condenser 104, a reflux drum 106, and a reboiler 108. The process plant may include a methanol synthesis unit containing at least one methanol synthesis reactor and a flash tank (not shown in FIG. 1) upstream of the distillation apparatus 100. The methanol synthesis unit is configured to at least partially react hydrogen and carbon oxides comprising carbon dioxide rich synthesis gas under methanol synthesis conditions and discharge a liquid crude methanol stream comprising methanol, water, dissolved synthesis gas components, and low-boiling byproducts from the methanol synthesis unit.

The flash tank is configured to (i) receive the liquid crude methanol stream from the methanol synthesis unit, and (ii) discharge a liquid depressurized crude methanol stream, depleted in synthesis gas components, as a bottoms product and a gaseous overhead product stream comprising synthesis gas components. The distillation column 102 includes a crude methanol inlet 110, an overhead product outlet 118 at the top of the distillation column 102, a bottoms product outlet 112 at the bottom of the distillation column 102, and a first side draw 114. The distillation column 102 may comprise at least 30 theoretical plates, preferably at least 40 theoretical plates. The first side draw 114 is located in the rectifying section of the distillation column 102. The first side draw 114 is arranged at most 10 theoretical plates, preferably at most 5 theoretical plates below the overhead product outlet 118. The crude methanol inlet 110 is configured to introduce the liquid depressurized crude methanol stream depleted in synthesis gas components into the distillation column 102. The distillation column 102 is configured to (i) separate crude methanol stream by distillation under distillation conditions, (ii) discharge an overhead product stream via the overhead product outlet 118, (iii) discharge a bottoms product stream via the bottoms product outlet 112, and (iv) discharge a pure methanol product stream via the first side draw 114. The overhead product stream comprises gaseous low-boiling point byproducts and synthesis gas components. The overhead product stream is condensed using the condenser 104. A first portion of the condensed overhead product stream is used as a fuel. A remaining portion of the condensed overhead product stream is directed into the reflux drum 106 which is recycled back to the top of the distillation column 102 to provide cooling and condensation of the up-flowing overhead product stream. The bottoms product stream includes water and is enriched with respect to its water content relative to the liquid crude methanol stream. The bottoms product stream is heated in a reboiler 108 and recycled back to the bottom of the distillation column 102. The distillation column 102 further comprises a second side draw 116 which is arranged in a stripping section of the distillation column 102. The second side draw 116 is arranged at most 10 theoretical plates, preferably at most 5 theoretical plates above the bottoms product outlet 112. The distillation column 102 is configured to discharge a high-boiling product stream containing ethanol via the second side draw 116. The high-boiling product stream may include impurities and/or byproducts.

Figure 2:
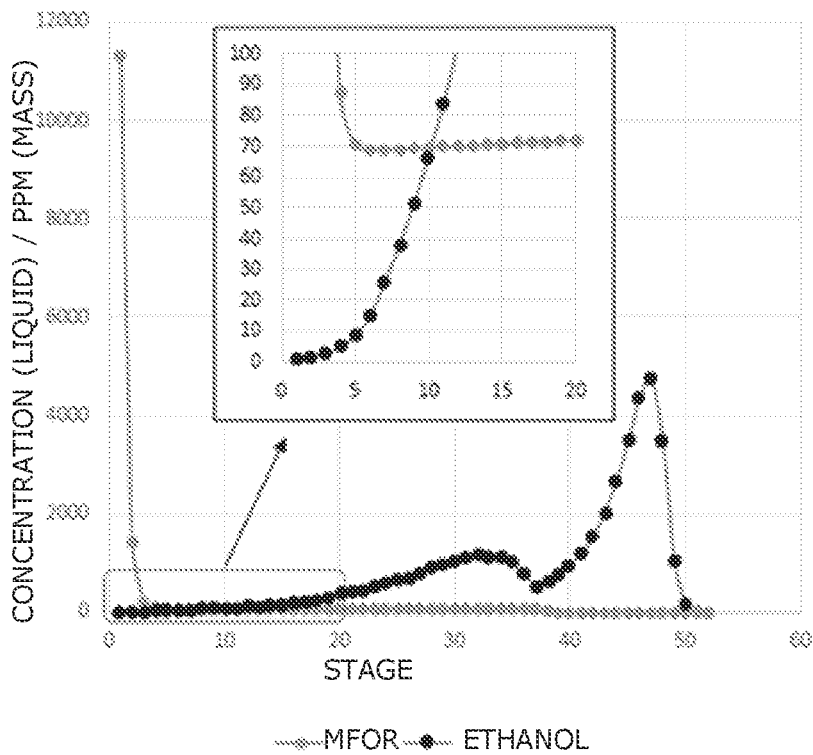
FIG. 2 is an exemplary graphical illustration that shows a concentration curve for ethanol and methyl formate (MFOR) as a function of theoretical plates (stages) in a distillation apparatus consisting of a single distillation column according to an embodiment of the present disclosure.

FIG. 2 is an exemplary graphical illustration that shows a concentration curve for ethanol and methyl formate (MFOR) as a function of theoretical plates (stages) in a distillation apparatus consisting of a single distillation column according to an embodiment of the present disclosure. In the exemplary graphical representation, a number of theoretical plates (stages) is plotted in a X-axis and concentration of ethanol and methyl formate (MFOR) is plotted in a Y-axis. With reference to the exemplary graph illustration, a limit concentration for ethanol is reached from stage 5 onwards, although the concentration of methyl formate also increases sharply (70-90 weight (wt.)-parts per million (ppm)). Methyl formate is by far the most strongly occurring byproduct in crude methanol. In general, methyl formate is believed to affect the acidity of methanol through the following reaction (ester hydrolysis into methanol and formic acid):

$$
\underset{\substack{H}}{\overset{O}{\underset{\|}{C}}}\!\!-\!OH \;+\; HO\!-\!CH_3 \;\underset{}{\overset{H^{\oplus}}{\rightleftharpoons}}\; \underset{\substack{H}}{\overset{O}{\underset{\|}{C}}}\!\!-\!O\!-\!CH_3 \;+\; H_2O
$$

In the laboratory, methanol with a methyl formate concentration of 500 wt.-ppm is tested for acidity according to ASTM D1613-06 (2012) procedure and the acidity is found to be between 0.7 and 2.2 wt. ppm. The Grade AA specification limit for acidity is 30 ppm (mass). The measured values are close to a detection limit of the analytical method employed. Thus, the specifications of a Grade AA methanol (Methanol purity grades according to US FEDERAL SPECIFICATION METHANOL (METHYL ALCOHOL), O-M-232N (8 Feb. 2016)) can be met by the single distillation column with a side draw of the present disclosure. The below table shows the chemical and physical characteristics of grades A and AA methanol.

For grade AA only, convert the concentration of ethanol in microgram ($\mu$g)/gram (g) to percent by weight ethanol.

| Characteristics | Requirements | | Test paragraph/ |
| --- | --- | --- | --- |
| | Grade A | Grade AA | method |
| Acetone, percent by mass, maximum | 0.003 | 0.002 | 4.3.1.1 |
| Acidity (as acetic acid), percent by mass, maximum | 0.003 | 0.003 | ASTM E346 |
| Appearance | Free of opalescence, suspended matter and sediment | Free of opalescence, suspended matter and sediment | 4.3.1.2 |
| Carbonizable impurities, color, Platinum-Cobalt (Pt-Co), maximum | No. 30 | No. 30 | ASTM E346 |
| Color, Pt-Co, maximum | No. 5 | No. 5 | ASTM E346 |
| Distillation range at 760 mm, maximum | 1.0° C. (and shall include 64.6 ± 0.1° C.) | 1.0° C. (and shall include 64.6 ± 0.1° C.) | ASTM E346 |
| Ethanol, percent by mass, maximum | — | 0.001 | ASTM E346[1] |

-continued

| | Requirements | | Test paragraph/ |
|---|---|---|---|
| Characteristics | Grade A | Grade AA | method |
| Nonvolatile matter, mg per 100 mL, maximum | 10 | 10 | ASTM D1353 |
| Odor | Characteristic, non-residual | Characteristic, non-residual | ASTM D1296 |
| Permanganate time | No discharge of color in 30 minutes | No discharge of color in 30 minutes | ASTM E346 |
| Specific gravity at 20/20° C., maximum | 0.7928 | 0.7928 | ASTM E346 |
| Water, percent by mass, maximum | 0.15 | 0.10 | ASTM E346 |

FIGS. 3A-3C are flowcharts illustrating a process for producing pure methanol from a carbon dioxide-rich synthesis gas containing hydrogen and carbon oxides as synthesis gas components according to an embodiment of the present disclosure. At a step 302, hydrogen and carbon oxides comprising carbon dioxide rich synthesis gas are at least partially reacted under methanol synthesis conditions in a methanol synthesis unit containing at least one methanol synthesis reactor. At a step 304, a liquid crude methanol stream comprising methanol, water, dissolved synthesis gas components, and low-boiling byproducts is discharged from the methanol synthesis unit. At a step 306, the liquid crude methanol stream is introduced into a flash tank, thereafter a liquid depressurized crude methanol stream, depleted in synthesis gas components, as a bottoms product and a gaseous overhead product stream comprising synthesis gas components are discharged from the flash tank. At a step 308, the liquid depressurized crude methanol stream depleted in synthesis gas components is introduced into a distillation apparatus consisting of a single distillation column, the distillation column comprising a crude methanol inlet, an overhead product outlet at the top of the distillation column, a bottoms product outlet at the bottom of the distillation column, and a first side draw, the first side draw is located in a rectifying section of the distillation column. At a step 310, the crude methanol stream is separated by distillation in the distillation column under distillation conditions. At a step 312, an overhead product stream is discharged via the overhead product outlet, the overhead product stream comprises gaseous low-boiling point byproducts and synthesis gas components. At a step 314, a bottoms product stream is discharged via the bottoms product outlet, the bottoms product stream comprises water and is enriched with respect to its water content relative to the liquid crude methanol stream. At a step 316, a pure methanol product stream is discharged via the first side draw.

Modifications to embodiments of the present disclosure described in the foregoing are possible without departing from the scope of the present disclosure as defined by the accompanying claims. Expressions such as "including", "comprising", "incorporating", "have", "is" used to describe, and claim the present disclosure are intended to be construed in a non-exclusive manner, namely allowing for items, components or elements not explicitly described also to be present. Reference to the singular is also to be construed to relate to the plural.

LIST OF REFERENCE NUMERALS

100—Distillation apparatus
102—Distillation column

104—Condenser
106—Reflux drum
108—Reboiler
110—Crude methanol inlet
112—Bottoms product outlet
114—First side draw
116—Second side draw
118—Overhead product outlet It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing pure methanol from a carbon dioxide-rich synthesis gas containing hydrogen and carbon oxides as synthesis gas components, comprising:

(a) at least partially reacting the hydrogen and carbon oxides comprising carbon dioxide rich synthesis gas under methanol synthesis conditions in a methanol synthesis unit containing at least one methanol synthesis reactor, wherein the carbon dioxide rich synthesis gas comprises a concentration of carbon dioxide of at least 15 mol-%, (b) discharging a liquid crude methanol stream comprising methanol, water, dissolved synthesis gas components, and low-boiling byproducts from the methanol synthesis unit, (c) introducing the liquid crude methanol stream into a flash tank, discharging from the flash tank a liquid depressurized crude methanol stream, depleted in synthesis gas components, as a bottoms product and a gaseous overhead product stream comprising synthesis gas components, (d) introducing the liquid depressurized crude methanol stream depleted in synthesis gas components into a distillation apparatus consisting of a single distillation column, the distillation column comprising a crude methanol inlet, an overhead product outlet at the top of the column, a bottoms product outlet at the bottom of the column, and a first side draw, wherein the first side draw is located in the rectifying section of the distillation column, (e) separating the crude methanol stream by distillation in the distillation column under distillation conditions, (f) discharging an overhead product stream via the overhead product outlet, wherein the overhead product stream comprises gaseous low-boiling point byproducts and synthesis gas components, (g) discharging a bottoms product stream via the bottoms product outlet, wherein the bottoms product stream comprises water and is enriched with respect to its water content relative to the liquid crude methanol stream, and (h) discharging a pure methanol product stream via the first side draw, wherein the pure methanol product stream comprises a methanol concentration of at least 99.85 wt-% on a dry basis.

2. The process according to claim 1, wherein the carbon dioxide-rich synthesis gas comprises a concentration of carbon monoxide, and a concentration of carbon dioxide, and the concentration of carbon dioxide is greater than the concentration of carbon monoxide.

3. The process according to claim 2, wherein the carbon dioxide-rich synthesis gas the concentration of carbon monoxide is at most 4 mol.-%.

4. The process according to claim 1, wherein the carbon dioxide-rich synthesis gas comprises a stoichiometry number, and the stoichiometry number of the carbon dioxide-rich synthesis gas is between 1.8 and 2.4.

5. The process according claim 1, wherein the crude methanol comprises methyl formate, and a concentration of methyl formate in the crude methanol is at most 2000 wt.-ppm.

6. The process according to claim 1, wherein the distillation column comprises at least 30 theoretical plates.

7. The process according to claim 1, wherein the distillation column is operated at 1 to 5 bara.

8. The process according to claim 1, wherein the first side draw is arranged at most 10 theoretical plates below the overhead product outlet.

9. The process according to claim 1, wherein the distillation column comprises a second side draw, wherein the second side draw is arranged in the stripping section of the distillation column.

10. The process according to claim 9, wherein the second side draw is arranged at most 10 theoretical plates above the bottoms product outlet (112).

11. The process according to claim 9, wherein an ethanol containing high-boiling product stream is discharged from the distillation column via the second side draw.

12. The process according to claim 11, wherein the high-boiling product stream comprises ethanol, and the ethanol concentration in the high-boiling product stream is at most 10 mol.-%.

13. The process according to claim 11, wherein the methanol concentration in the high-boiling product stream is at least 25 mol.-%.

* * * * *